Figure 1:
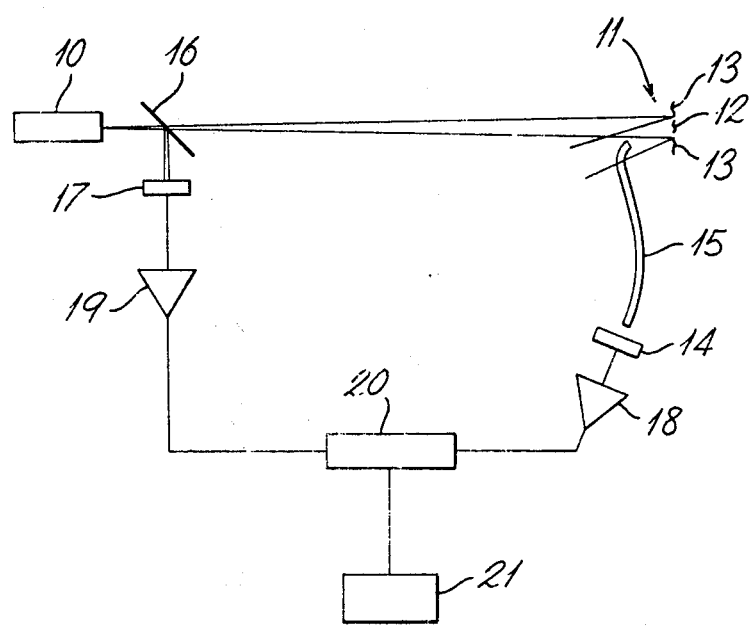

United States Patent [19]

Anson et al.

[11] 4,339,954
[45] Jul. 20, 1982

[54] MEASUREMENT OF SMALL MOVEMENTS

[75] Inventors: Michael Anson; Shin-Ho Chung, both of London, England; Alan G. Pettigrew, Homebush, Australia

[73] Assignee: National Research Development Corporation, London, England

[21] Appl. No.: 179,287

[22] PCT Filed: Mar. 9, 1979

[86] PCT No.: PCT/GB79/00043

§ 371 Date: Nov. 9, 1979

§ 102(e) Date: Oct. 29, 1979

[87] PCT Pub. No.: WO79/00841

PCT Pub. Date: Oct. 18, 1979

[30] Foreign Application Priority Data

Mar. 9, 1978 [GB] United Kingdom ............... 09398/78

[51] Int. Cl.$^3$ ............................................... G01B 9/02
[52] U.S. Cl. ....................................... 73/657; 128/665; 128/746
[58] Field of Search .................... 73/655, 657, 643; 128/665, 746; 356/349, 358

[56] References Cited

U.S. PATENT DOCUMENTS 4,009,707  3/1977  Ward ................................... 128/746
4,180,328  12/1979 Drain ................................... 73/657

FOREIGN PATENT DOCUMENTS 2155853  5/1973  Fed. Rep. of Germany ........ 73/657

OTHER PUBLICATIONS

K. J. Ebeling, "Measurement of In-Plane Mechanical Vibrations in the Sub-Angstrom Range by Use of Speckle Imaging", *Optics Communications*, vol. 24, No. 1, pp. 125-128, Jan. 1978.

U. Köpf, "Use of Television Apparatus in Optico-Coherent Measurement of Mechanical Vibrations in the $\mu$m. Range", *Messtechnik*, vol. 80, No. 4, pp. 105-108, Apr. 1972.

F. P. Chiang et al., "Dynamic Laser Speckle Interferometry Applied to Transient Flexure Problem", *Applied Optics*, vol. 16, No. 12, pp. 3085-3086, Dec. 1977.

G. J. Jako et al., "Use of a New Photoelectric Device (Fotonic Sensor) for Vibration Measurements in the Ear", *Journal Acoustical Soc. Am.*, vol. 40, No. 5, p. 1263, Nov. 1966.

"Dynamic Statistical Properties of Vibrating Laser Speckle in the Diffraction Field", by N. Takai, et al., Applied Optics, vol. 17, No. 23, Dec. 1, 1978.

*Primary Examiner*—Stephen A. Kreitman
*Attorney, Agent, or Firm*—Cushman, Darby & Cushman

[57] ABSTRACT

Measurement of small oscillatory movements of an irregular surface involves the production of a speckle pattern therefrom by coherent light illumination, and the arrangement of a photodetector for direct response to such pattern, variations in photodetector output component at the frequency of the surface movement representing that movement. Another, stationary, illuminated irregular surface can be involved to produce a speckle interference pattern for response of the photodectector thereto and, in the case where the two surfaces are closely adjacent, a single beam can be used to illuminate the first and other surfaces predominantly and by stray light, respectively. This common beam illumination can be used in prior speckle interferometry. The first surface can be an eardrum oscillated by a sound wave, suitably of swept frequency or impulse form, with detection of the photodetector variations respectively being in synchronous manner or by Fourier analysis, respectively.

14 Claims, 2 Drawing Figures

MEASUREMENT OF SMALL MOVEMENTS

This invention concerns the measurement of small movements and more particularly the measurement of movements, typically vibrations, having magnitudes less than the wavelengths of light.

Interferometry is a well-established technique for making such measurements and a more recently developed technique of this kind is that known as laser speckle interferometry. This last technique derives from the finding that the scattering and reflexion of coherent light from an irregular surface produces a field which can be imaged as a speckled pattern of relatively light and dark areas, and that two such fields from respectively different surfaces can interfere to produce a pattern which is modulated in phase upon movement of one of the surfaces in the direction of the incident light.

It is to be noted that a speckle pattern itself will be subject to variation together with movement of the surface from which it is derived, but this variation has previously been considered too random and/or fine grained to be of direct use. Indeed, early opinions of speckle pattern phenomena regarded the same as undesirable noise effects associated with laser illumination.

In any event, laser speckle interferometry as so far practised has entailed discrete recording in various ways of an imaged interference pattern created by one relative disposition of the two surfaces for comparison therewith of the directly corresponding pattern created by a changed disposition of the two surfaces in order to obtain a measure of the movement leading from one disposition to the other. The recording step of this procedure necessarily involves a complexity of equipment and/or processing compared to an intrinsically instantaneous measurement technique.

Also, laser speckle interferometry as so far practised has entailed the provision of separate beams of coherent light, often derived from a common laser source, to respectively illuminate the two surfaces. This involves a complexity of optical equipment and, possible more important, can render difficult or impracticable the application of the technique to surfaces to which access is difficult.

In contrast to the situation just described the present invention provides laser speckle interferometry techniques, and related techniques, which require no discrete recording of interference patterns and which can be operated with a single coherent light beam. The presently proposed techniques in fact have two aspects respectively associated with the advantages just mentioned and these two aspects are preferably, but not necessarily, deployed together in application of the invention.

According to one of these aspects of the invention there is provided a method of measuring the movement of an oscillating irregular surface, which comprises illuminating that surface with coherent light, arranging a photodetector for direct response to scattering and reflexions of said light from said surface, and employing from the output of said photodetector variations in the component thereof at the frequency of said movement to represent such movement.

This aspect of the invention derives from the finding that the photodetector has an amplitude-modulated component which corresponds to the surface movement. This finding arises when the oscillating surface is employed alone or in association with a similarly illuminated stationary surface, the photodetector being located in corresponding fields of both surfaces in the latter case, and also when the photodetector has a near or far field location relative to the surface or surfaces.

While a detailed analysis of this phenomenon has yet to be finalised, it is at present considered that the relevant modulated output component results from mixing at the photodetector of the scattered and reflected fields as these are converted to electrical signal form. Certainly, in the case when two surfaces are involved, the presence of an interference effect has been confirmed by employing a piezoelectric crystal as one surface and vibrating the same at known frequency and amplitude, to find that the relevant output component successively increases and decreases in sinusoidal manner with linearly increasing amplitude of vibration.

Also, another factor which is thought to be relevant to the above aspect of the invention in some circumstances is that the aforementioned random and fine-grained nature of speckle patterns involves a presumption that the originating surface is fully random in its irregularity, whereas in fact surfaces involved in many practical measurement situations will have a partially ordered structure by virtue of the way in which they are formed. This factor can heighten the optical relationships which give rise to the modulated component of interest.

The provision of apparatus adapted to carry out the above proposed method is also contemplated within this first aspect of the invention.

A second aspect of the invention derives from the consideration that, in the case where two surfaces are involved, detection of the output component of interest can be effected when this component constitutes as little as 0.1% of the total photodetector output signal and that the provision of separate illuminating beams of similar intensities for the two surfaces is not necessary. Indeed, since the photodetector employed according to the invention in its first aspect converts the light patterns incident thereon from an electric field representation to an electric current representation, the contribution to the patterns from one of the surfaces can be as little as the order of $10^{-6}$ times that from the other surface. Moreover, this consideration can be equally relevant to previously known forms of laser speckle interferometry, and particularly those which employ a discrete pattern transducer such as a television camera tube for the purposes of the recording step.

Given this consideration the present invention, in its second aspect, provides a laser speckle interferometry method or apparatus in which one of the two irregular surfaces is illuminated by stray coherent light from a beam thereof directed predominantly at the other of said surfaces.

Figure 2:
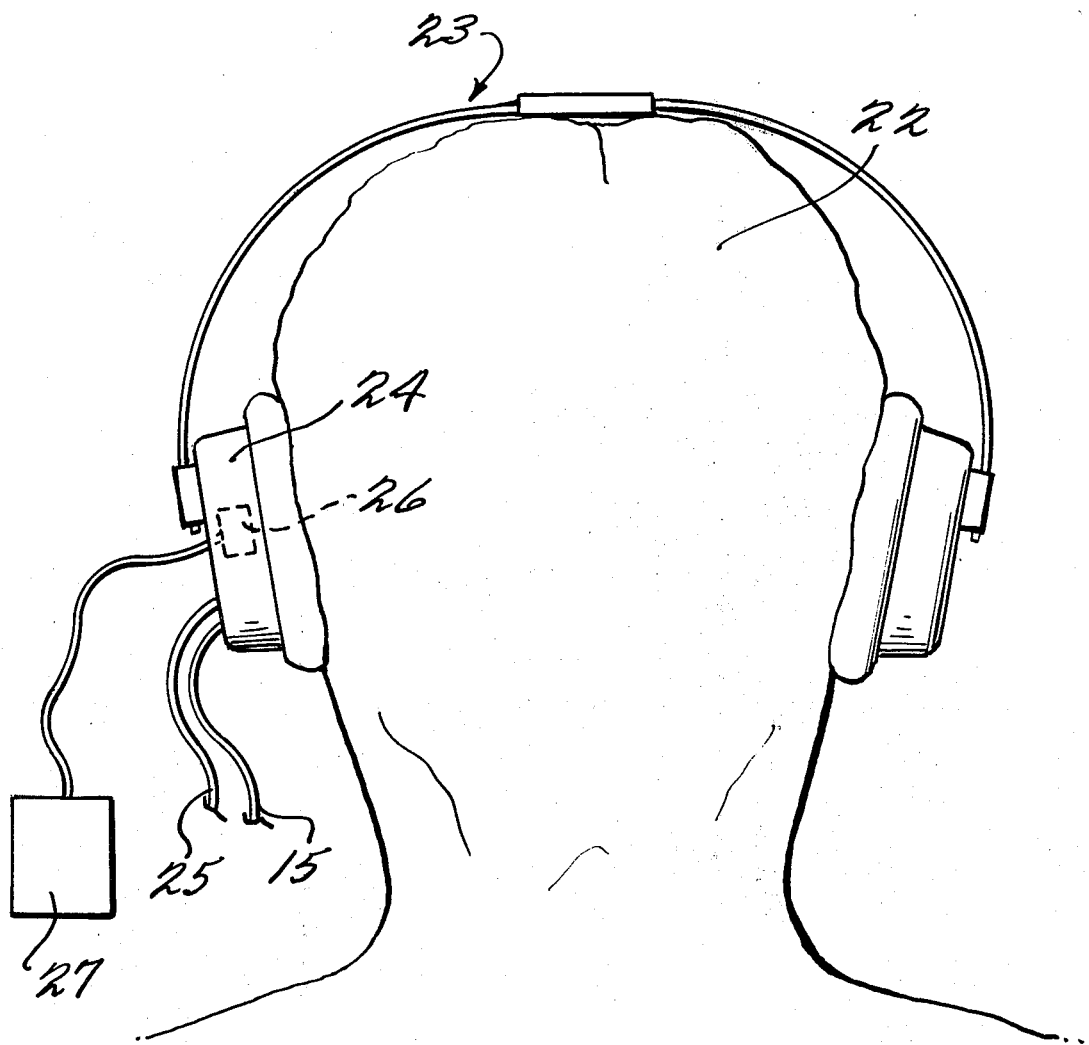

In order that the above discussed aspects and other preferred features of the invention may be more fully understood, the same will now be described by way of example with reference to the accompanying drawings, wherein:

FIG. 1 schematically illustrates one embodiment of apparatus employed in initial development of the invention in a study of the dynamics of the amphibian ear, and FIG. 2 illustrates elements of the invention configured for application to the human ear.

The illustrated embodiments in fact represent apparatus employed in initial development of the invention in a study of the dynamics of the amphibian middle ear.

The embodiment comprises a polarised He-Le laser source 10 of 2 mW power output and wavelength, λ, of 632.8 nm having its output beam directed at an object 11 which includes a vibratable surface 12 and an adjacent or surrounding, relatively fixed surface 13. In the initial development the surface 12 has been the tympanum of a frog, and the surface 13 the surrounding tissue covering the adjacent bone structure. The laser beam is directly predominantly at the surface 12 but has sufficient divergence for stray light to be incident on an area of the surface 13.

Scatter and reflexion from both surface is monitored by a photodiode 14, this light field being applied to the photodiode by way of a fibre optic light guide 15 having its collecting end located in the near field of the surfaces 12 and 13.

A beam splitter 16 is located near the output mirror of the source 10 and directs a proportion, suitably about 10%, of the output beam on to a second photodiode 17.

The photodiode outputs are applied, through respective current-to-voltage amplifiers 18 and 19, to a voltage divider 20 which divides the first photodiode output by the second. This operation reduces the effective amplitude fluctuations of the laser source by greater than 100-fold.

The divider output is applied to a spectrum analyser 21 or some other means for detecting, among others, the output component at the frequency of vibration of surface 12.

In the use of the illustrated embodiment the resonance characteristic of the frog's middle ear has been determined by application of successively different and frequencies to vibrate the eardrum and employing the output component at the corresponding frequencies from the spectrum analyser as a measure of the amplitude of vibration.

The present view of the basis for this procedure is that, when the surface 12 undergoes sinusoidal vibrations with amplitude $a_o$ at angular frequency $w_a$, the current at the photodiode 14 is represented as $$I = \sigma[<E_S \cdot E_S^*> + <E_r E_r^*> + 2|E_S| \cdot |E_r| \cos\{4\pi a_o/\lambda \cdot \sin(w_a t + \phi)\}]$$

where $\sigma$ is the photodiode responsivity, $E_s$ and $R_r$ are the total electric fields at the photodiode respectively due to the surfaces 12 and 13, and $\phi$ is an arbitrary phase between these fields due to the vibrations. The last term of this equation can be expanded as a series of Bessel functions and the component at the fundamental frequency $w_a$ can be determined by the analyser such that $$I(w_a) = \sigma\{|E_S| \cdot |E_r| J_1(4\pi a_o/\lambda) \sin w_a t \cdot \sin \phi\}$$

where $J_1$ is a Bessel function of the first kind and first order with argument $4\pi a_o/\lambda$. The average value of sin $\phi$ after full wave rectification by the analyser is $2/\pi$, and the function $J_1$ has a maximum value at argument 1.841 radians and is zero at 3.84 radians. Thus, the output component of interest will be a maximum for vibration of the surface 12 with a peak-to-peak displacement of 185 nm, and a minimum for peak-to-peak displacement of 386 nm. This analysis is considered to be correct within 5% provided that the angle between the incident and scattered beams is less than 36°.

As noted earlier the present theoretical consideration of the invention has been confirmed by the use of a piezoelectric crystal as the vibrating surface. In fact this has been done with the crystal and its surrounding structure in place of the surface 12 and 13 of the illustrated embodiment, and this has verified the above predictions. Moreover, from a series of measurements using the crystal, it has been concluded that the limit of resolution is about 0.2 nm, and that the response is approximately a linear function of displacement up to 1/10 of the wavelength of red light.

While the invention has clearly been developed initially for the purposes of an academic study, it is not limited thereby. Indeed the introductory discussion above makes it equally clear that the invention offers advantage relative to existing laser speckle interferometry and the invention is obviously applicable in at least similar circumstances to those of the prior techniques.

However, it is to be noted that further development of the invention concerns application thereof for clinical audiometric purposes to monitor tympanic membrane movement and assess inner ear condition. The invention is well suited to this application in that it can provide a procedure which, contrary to existing procedures, requires little or no co-operation or comprehension on the part of the patient. Moreover, again in contrast to existing procedure such as tympanic acoustic impedance measurement, application of the present invention does not require sealing of the external ear canal or any other such operation which applies an abnormal constraint to the middle ear; in other words the invention can be employed to measure wholly unconstrained tympanum displacement in response to applied sound.

Naturally in the application of the invention under discussion, some means will be provided for applying sound into the ear. This can take any suitable form, but in one preferred form involves a sound source operable at successively changing frequency by a swept oscillator or equivalent device. In this event the output detector should be of locked variable frequency form, such as a spectrum analyser/tracking generator combination or a sweep generator/dynamic lock-in detector system. In an alternative arrangement the sound stimulation for the ear can be applied as a short impulse with the detector effecting Fourier analysis. This alternative may be advantageous in involving a shorter exposure of the ear to the laser source, and also in providing output signals indicating the damping properties of the middle ear in addition to resonant properties.

The necessary apparatus interfacing with the patient may conveniently comprise an earphone-like structure housing a miniature sound source of the kind such as used in hearing aids, or a spark gap or other form of sonic impulse generator. The fibre optic guide can extend through this structure between the external ear canal and photodiode, and a further such guide can be employed to pass the laser beam into the canal, or the structure can be apertured for this purpose.

The outgoing light guide can comprise a single fibre or a multiple fibre system. In the latter case the fibres or sub-sets thereof can be directed to respectively different photodiodes to enhance the detected signal or to allow analysis to be effected in respect of additional output signal components such as those at harmonics of the frequencies of interest.

Similarly, any in-going light guide can comprise a single or multiple fibre system, and in the latter case the proximal ends of the fibres can be employed to direct light on to respectively different areas of the vibrated and stationary surfaces. This may improve the output signal by the effective application of separate beams on to the two surfaces, and/or it may allow differential assessment of the condition of the tympanum by effective application of a plurality of beams on to respectively different areas thereof.

An arrangement suitable for application to the human ear is schematically illustrated in FIG. 2. Reference numeral 22 represents the head of a patient wearing an earphone-like structure 23 with one earpiece 24 havig the output fibre optic light guide 15 and an input guide 25 passing therethrough. In addition the earpiece 24 houses a second source 26 operable by a remote signal generator 27 connected thereto, the generator providing a swept frequency or pulse input.

While the invention has been described in connection with what is presently considered to be the most practical and preferred embodiments, it it to be understood that the invention is not to be limited to the disclosed embodiments but on the contrary, is intended to cover various modifications and equivalent arrangements included within the spirit and scope of the appended claims which scope is to be accorded the broadest interpretation so as to encompass all such modifications and equivalent structures.

We claim:

1. A method of measuring the out of plane movement of an oscillating irregular surface, comprising the steps of:
    illuminating the surface with coherent light, the reflexions and scattering of the coherent light from the surface forming a speckle pattern,
    detecting with a spatially integrating photodetector, variations caused by the out-of-plane movement in the speckle pattern and generating a photodetector signal indicative thereof and
    continuously detecting, from the photodetector signal, amplitude variations thereof at the frequency of the out-of-plane movement to represent such movement.

2. A method according to claim 1 further comprising the steps of:
    illuminating another, stationary, irregular surface with coherent light, and
    detecting variations in a speckle interference pattern produced by scattering and reflexions from both said surfaces, by arranging said photodetector for direct response to said interference pattern.

3. A method according to claim 2 characterised in that said surfaces are closely adjacent, and in that said other surface is illuminated by stray coherent light from a beam thereof directed predominantly at the first-mentioned surface.

4. A method according to claim 1, 2 or 3 characterised in that the first-mentioned surface is a tympanum oscillated by a predetermined sound wave applied thereto.

5. A method according to claim 4 characterised in that said sound wave is of swept frequency form and said variations are detected in a locked-frequency manner.

6. A method according to claim 4 characterised in that said sound wave is of impulse form and said variations are detected by Fourier analysis.

7. A method of measuring the movement of an oscillating surface, comprising the steps of:
    illuminating the oscillating surface with a beam of coherent light,
    illuminating a second, stationary, irregular surface, by stray coherent light from both of said beam directed predominantly at said oscillating surface, the scattering and reflexions of coherent light from said surfaces forming a speckle interference pattern, and
    detecting using a photodetector variations in the speckle interference pattern.

8. Apparatus for measuring the movement of an oscillating irregular surface comprising:
    a coherent light source for illuminating the oscillating surface, and
    means for detecting variations caused by said movement in a speckle pattern produced by scattering and reflexions of light from said surface,
    said detecting means including a spatially integrating photodetector arranged for direct response to said pattern, and a detector continuously responsive to amplitude variations in an output signal of said photodetector at the frequency of said movement.

9. Apparatus according to claim 8, further including another spatially-integrating photodetector for direct response to light from said source, and a signal divider responsive to outputs from both photodetectors for supplying an input for said detector.

10. Apparatus according to claim 8 or 9 characterised by a sound generator for applying a predetermined sound wave to oscillate said surface.

11. Apparatus according to claim 10 characterised in that said sound generator is of swept frequency form, and in that said detector is operably frequency-locked with said generator.

12. Apparatus according to claim 10 characterised in that said sound generator is of impulse form, and in that said detector effects Fourier analysis.

13. Apparatus according to claim 10, characterised by an earphone-form device housing at least part of said sound generator to apply the output thereof to a tympanum.

14. Apparatus according to claim 13 characterised in that said device has at least one fibre optic guide passing therethrough to convey said illuminating light to said surface and/or said pattern to the first-mentioned photodetector.

* * * * *